July 2, 1957 M. J. MURRAY Plant Pat. 1,614

MINT PLANT

Filed Sept. 1, 1955

INVENTOR.
MERRITT J. MURRAY
BY Lindley E. Miller

United States Patent Office

Plant Pat. 1,614
Patented July 2, 1957

1,614

MINT PLANT

Merritt J. Murray, Kalamazoo, Mich., assignor to A. M. Todd Company, Kalamazoo, Mich., a corporation of Michigan Application September 1, 1955, Serial No. 532,130

1 Claim. (Cl. 47—59)

Figures 1, 2:
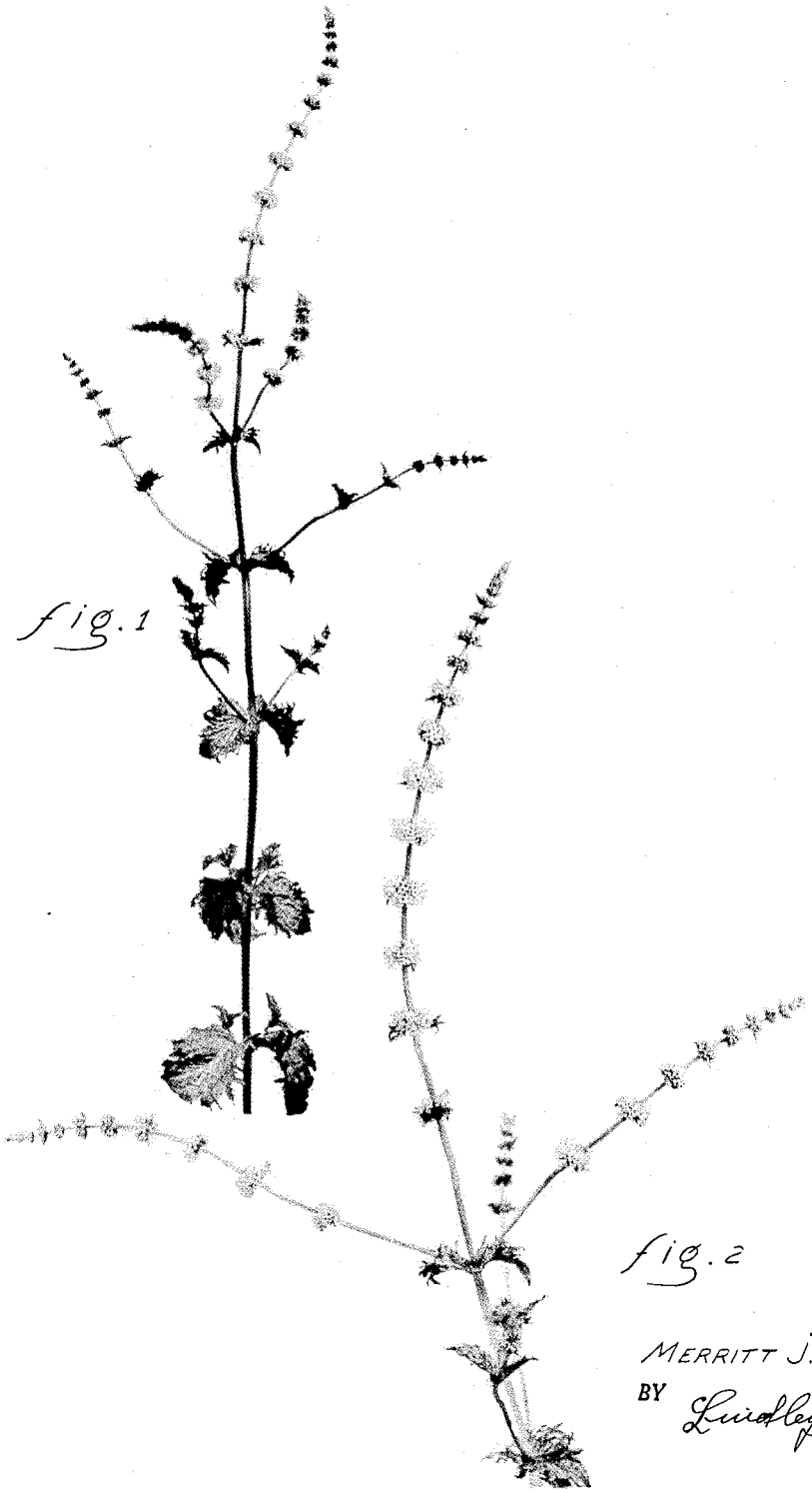

This invention relates to a new and distinct variety of mint plant which was initially produced by hybridization between *Mentha arvensis* L. *piperascens* Briq. and *Mentha crispa* L. (*Mentha spicata* L. var. *crispata*) and thereafter asexually reproduced from stolons at nurseries near Kalamazoo, Michigan.

The distinctive characteristics of the new variety comprise its generally quite erect and branching habit, its hybrid vigor and its somewhat greater size than either *Mentha arvensis* L. *piperascens* Briq. or *Mentha crispa* L. The new variety generally grows to a height of about two and one-half feet when cultivated under field conditions. The stems are coarser than those of either parent and the plant is much less fragile than *Mentha arvensis* L. *piperascens* Briq. The new variety is extremely hardy under southern Michigan and central Washington conditions. It is especially characterized by the high total menthol content of its oil. The colors of the plant and flowers are not distinctive and resemble closely those of other mint varieties when grown under comparable conditions.

The leaves of the new variety are opposite, broadly ovate and much wrinkled and curled. The portions of the leaves between the veins are indented upwardly, forming deep depressions on the under sides of the leaves. The leaves are deeply serrated, often to the extent of three-eighths inch or more, the lobes between the serrations being narrow and curled. The leaves are only very slightly hairy on the under sides of the ribs while the stems are smooth with very few sparse hairs. The flowers are borne in the form of axillary globular clusters, the leaves on the flower stems being very small and giving the appearance of small spikes.

The new variety is immune to spearmint rust frequently identified as *Puccina menthae*, and is highly resistant to powdery mildew, *Erysiphe cichoraccarum* D. C., and to leaf spot diseases, including *Cephalosporium sp.*, which attack *Mentha arvensis* L. *piperascens* Briq. The variety matures earlier than *Mentha arvensis* L. *piperascens* Briq.

The resistance of the new variety to these organisms was demonstrated in field plots on upland soil near Mentha, Michigan. Disease conditions were accentuated by interplantings of *M. arvensis* L. *piperascens* Briq., and of *M. citrata* Ehrh., *M. piperita* L., *M. cardiaca* (Gerarde or Baker?), *M. spicata* L. and other susceptible wild species as well as of a number of susceptible hybrid varieties under test. Mildew conditions were accentuated by shaking and spreading greenhouse grown *M. arvensis* L. *piperascens* Briq. heavily infested with powdery mildew over the plot. A similar second plot was planted the next year adjacent the first with stock taken from the first plot. The first year's plot was left unplowed, the plants in it being permitted to grow undisturbed the second year to furnish additional continuing inoculation of the second plot.

Susceptible varieties in both plots, including *M. arvensis* L. *piperascens* Briq., were heavily infested with mildew and leaf spot diseases, including *Cephalosporium sp.* Spearmint rust infestation was heavy in both plots, the susceptible varieties becoming 90 to 100 percent defoliated. The new variety was not attacked by spearmint rust in either plot and only to an insignificant extent by powdery mildew and leaf spot diseases.

Similar test procedures as regards powdery mildew and leaf spot diseases were carried out near Toppenish, Washington, under conditions of both overhead and ditch irrigation with comparable results.

The new variety is particularly remarkable for the high total menthol content of its oil as compared with *Mentha piperita* L. and other varieties of mint suitable for field cultivation under southern Michigan and central Washington conditions. This is all the more remarkable since one of the parents, *Mentha crispa* L., is a wild spearmint, the oil of which contains practically no menthol. The oil of the new variety usually contains from 75 to 83 percent total menthol as determined by the method for total menthol content given in the United States Pharmacopoeia No. 14.

In the drawings, which are photographic illustrations of the new variety:

Figure 1 is a view of a representative branch of the new variety showing the general arrangement and form of the leaves, stems and flowers, and Figure 2 is an enlarged view of a flower stem showing the small nature of the leaves on the flower stems.

The hybridization leading to the new variety was carried out in the summer of 1951 in southern Michigan. The seed resulting from the hybridization was planted and grown in the spring and summer of 1952. The new variety was selected from among a large number of other hybrids as being of commercial value and was first asexually reproduced in southern Michigan in the spring of 1953. It has been grown by asexual reproduction in southern Michigan and in central Washington since that time. It has consistently exhibited its hardy characteristics and the high total menthol content of its oil referred to previously in both localities.

I claim:

A new and distinct variety of mint plant substantially as described, characterized by its hardy nature, its non-fragile nature as compared with *Mentha arvensis* L. *piperascens* Briq., by its curled, indentated and deeply serrated leaves and by the high total menthol content of its oil as compared with *Mentha piperita* L.

No references cited.